United States Patent [19]

Satake

[11] Patent Number: 5,144,954
[45] Date of Patent: Sep. 8, 1992

[54] ULTRASONIC DIAGNOSING APPARATUS

[75] Inventor: Nozomi Satake, Nishinasunomachi, Japan

[73] Assignee: Kabushiki Kaisha Toshiba, Asaki, Japan

[21] Appl. No.: 548,390

[22] Filed: Jul. 5, 1990

[30] Foreign Application Priority Data

Jul. 6, 1989 [JP] Japan .................. 1-174426

[51] Int. Cl.⁵ .................................. A61B 8/06
[52] U.S. Cl. .................. 128/661.09; 128/661.01
[58] Field of Search .............. 128/660.01, 660.08, 128/661.01, 661.09, 660.05; 73/861.25

[56] References Cited

U.S. PATENT DOCUMENTS

| | | | |
|---|---|---|---|
| 4,542,746 | 9/1985 | Takamizawa | 128/660.08 |
| 4,817,614 | 4/1989 | Hassler et al. | 128/660.05 |
| 4,888,694 | 12/1989 | Chesarek | 128/660.01 |
| 4,890,267 | 12/1989 | Rudolph | 128/661.01 |
| 4,966,151 | 10/1990 | Takeuchi | 128/660.05 |
| 4,972,838 | 11/1990 | Yamazaki | 128/661.09 |
| 4,993,417 | 2/1991 | Seo | 128/661.09 |
| 5,014,710 | 5/1991 | Maslak et al. | 128/660.05 |
| 5,031,628 | 7/1991 | Nakamura et al. | 128/661.09 |
| 5,035,245 | 7/1991 | Nakamura et al. | 128/661.09 |

FOREIGN PATENT DOCUMENTS 64-43237 2/1989 Japan .

Primary Examiner—Francis Jaworski
Assistant Examiner—George Manuel
Attorney, Agent, or Firm—Cushman, Darby & Cushman

[57] ABSTRACT

An ultrasonic diagnosing apparatus is disclosed which performs transmission/reception of an ultrasonic wave with respect to an object by using an ultrasonic transducer, detects a Doppler shift signal from a reception signal, and displays ultrasonic data based on the data obtained by frequency-analyzing the Doppler shift signal. The apparatus includes a control section. The control section controls at least a transmitter/receiver so as to sequentially scan a plurality of ultrasonic beam scanning lines as a group. In addition, the control section performs group scanning by sequentially changing the ultrasonic beam scanning lines selected as the group while repeating sequential scanning within the group, thus performing beam scanning of the entire scanning region, thereby decreasing the sampling frequency for Doppler data without changing the pulse repetition frequency, and scanning in the scanning order of the ultrasonic beam with respect to the group, said scanning order corresponding to the group scanning direction of the ultrasonic beam scanning lines selected as the group.

24 Claims, 6 Drawing Sheets

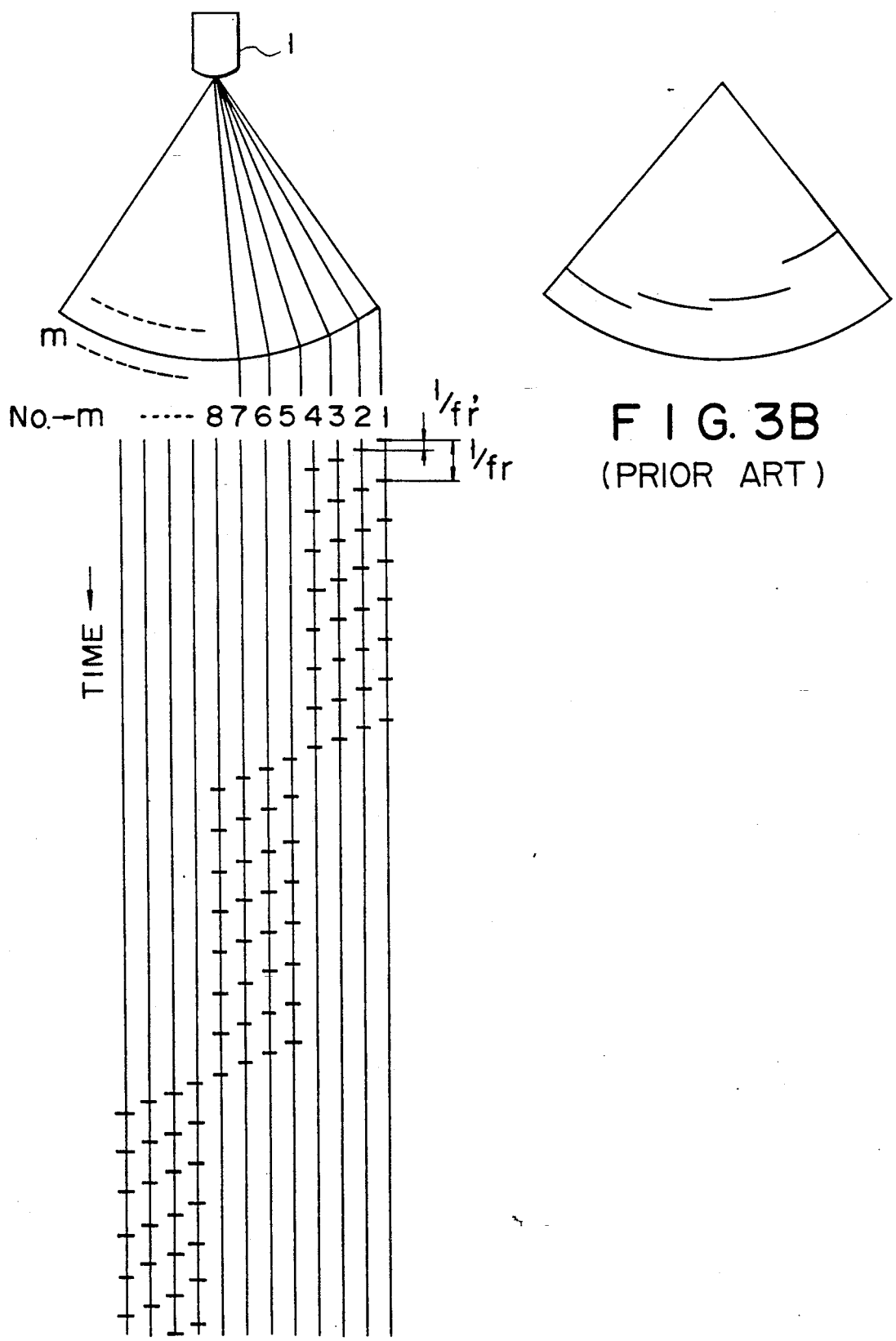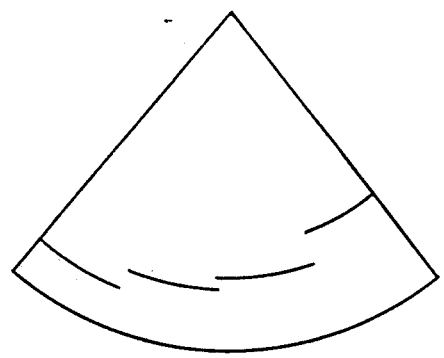
FIG. 3B (PRIOR ART)
FIG. 3A (PRIOR ART)

ECHO FROM OUTSIDE THE DEPTH OF VIEW FIELD

ULTRASONIC DIAGNOSING APPARATUS

BACKGROUND OF THE INVENTION

1. Field of the Invention

The present invention relates to an ultrasonic diagnosing apparatus for obtaining blood flow data as function information associated with the movement of tissues due to the function of an organ in a living body by utilizing an ultrasonic Doppler method, and for displaying the data as an image.

2. Description of the Related Art

A certain type of ultrasonic diagnosing apparatus is designed to obtain blood flow data by utilizing the ultrasonic Doppler method as well as a B-mode image (tomographic image) and an M-mode image, which are obtained by transmitting/receiving an ultrasonic wave to/from a living body as an object to be examined. In such an apparatus, measurement of a blood flow velocity based on the ultrasonic Doppler method is performed as follows. When an ultrasonic wave is transmitted to a blood flow in a living body, the ultrasonic wave is scattered by flowing blood cells. The ultrasonic echo obtained as the reflected ultrasonic wave is subjected to a Doppler shift due to the movement of blood cells upon reflection, and its frequency is changed. That is, if the center frequency of the transmitted ultrasonic wave is fc, the frequency of the ultrasonic echo subjected to a Doppler shift is changed by fd, and a frequency f of the received ultrasonic echo is given by:

$$f = fc + fd$$

In this case, the frequencies fc and fd are represented by the following equation:

$$fd = 2v\cos\theta \cdot fc/C$$

where
v: blood flow velocity
$\theta$: angle defined by ultrasonic beam and blood vessel
C: velocity of sound Therefore, the blood flow velocity v can be obtained by detecting the Doppler shift fd.

Two-dimensional image display of the blood flow velocity obtained in this manner is performed in the following manner.

Assume, as shown in FIG. 1, that scanning control of an ultrasonic wave based on so-called sector scan is performed by sequentially transmitting an ultrasonic beam as a pulse from an ultrasonic transducer 1 in respective directions D1, D2, D3, ... Dm. In sector scan by the ultrasonic transducer 1, in many cases, an array transducer in which a plurality of transducer elements are arranged is used, and a so-called sector electronic scan method is employed. In this method, transmission/reception of an ultrasonic wave by the plurality of transducer elements is repeated while the driving timings and/or processing timings of received signals of the respective transducer elements are sequentially and electronically shifted from each other, thus sequentially changing the steering angle of the ultrasonic beam to be transmitted/received. An ultrasonic transducer 1 and a linear scan method as a scanning control method thereof may also be employed. In this case, generally, a predetermined number of transducer elements of a plurality of ultrasonic transducer elements constituting an array transducer are used as a group. One transmission/reception operation of an ultrasonic beam is performed by using the group of transducer elements. By sequentially switching the transducer elements selected as the elements of the group, the transmission/reception position of the ultrasonic beam is horizontally moved. For example, the transducer elements of the group are sequentially shifted and selected one by one so as to electronically shift the transmission/reception position of the ultrasonic beam. In these scan operations, the excitation timings and/or reception signal timings of selected ultrasonic transducer elements located at central portion and a peripheral portion of the beam are shifted from each other so that the ultrasonic beam can be substantially focused by utilizing a difference in phase between sound waves generated by the respective transducer elements or reception signals thereof. This operation is called electronic focusing.

When blood flow data is to be obtained by the Doppler method, ultrasonic pulses are transmitted several times in a direction, e.g., the direction D1 in FIG. 1. The transducer 1 is driven by a transmitter/receiver 2 shown in FIG. 2 so as to transmit an ultrasonic wave into an object to be examined. The ultrasonic wave is then reflected by a blood flow (blood cells) in the object, and the reflected wave, i.e., the ultrasonic echo is received by the same transducer 1. This reflected ultrasonic wave is converted into an electrical signal by the transducer 1 and the transmitter/receiver 2.

The electrical signal is then phase-detected by a phase detector 3 so as to detect a Doppler shift signal. This Doppler shift signal is sampled at each of 256 sampling points SP set in the beam direction of the ultrasonic pulse. The Doppler shift signal at each sampling point SP is A/D (analog-to-digital)-converted by an MTI (moving target indicator) circuit 4a, and is subjected to MTI processing including frequency analysis. The obtained Doppler data is output to a DSC (digital scan converter) 6. The Doppler data is converted according to a scan system for display by the DSC 6 and is output to a display section 7.

In this manner, a blood flow velocity distribution in the direction D1 in FIG. 1 can be obtained as one-dimensional data in a real-time manner. A similar operation is repeated in the directions D2, D3, ... Dm, and one-dimensional data of a blood flow velocity distribution in each beam direction can be obtained. As a result, a two-dimensional blood flow image (blood flow velocity distribution image) is displayed on the display section 7.

The blood flow detection resolution (detection performance) at low velocity depends on the time length of data to be frequency-analyzed. If the sampling frequency of a Doppler signal is represented by fr, and the number of sampled data at one point is represented by n, a time length T of data to be frequency-analyzed is given by:

$$T = n/fr \tag{1}$$

In this case, a frequency resolution fd is given by:

$$fd = 1/T \tag{2}$$

Therefore, a lower limit fdmin of a measurable flow velocity is represented as follows:

$$fdmim = 1/T = fr/n \tag{3}$$

In order to detect a blood flow at low velocity, therefore, either the sampling frequency fr of a Doppler signal is reduced, or the number n of data is increased.

In two-dimensional Doppler imaging, however, $$FN \cdot n \cdot m \cdot (1/fr') = 1 \qquad (4)$$

(where FN: frame frequency; m: number of ultrasonic beam scanning lines; fr'; pulse repetition frequency or pulse rate frequency) The frame frequency FN is associated with the real time properties of a two-dimensional blood flow image and is normally 8 to 30. At this frequency, 8 to 30 frames can be obtained per second.

In the sector electronic scan method, if the number m of ultrasonic beam scanning lines (the number of scanning lines in the beam direction in ultrasonic scan) =32, the pulse repetition frequency fr'=4 kHz, and the number n of sampled data=8, the frame frequency FN is about 16.

A maximum depth of view field Dmax and the pulse repetition frequency fr' have the following relationship:

$$Dmax = C/(2 \cdot fr') \qquad (5)$$

If, therefore, the pulse repetition frequency fr' is increased in order to improve the detection resolution at low velocity, the maximum depth of view field cannot be increased. In addition, if the number m of ultrasonic beam scanning lines is decreased, the ultrasonic beam scanning line density is reduced, resulting in degradation of image quality.

If the detection resolution at low velocity is improved in this manner, other characteristics are degraded.

Under the circumstances, for example, Published Unexamined Japanese Patent Application No. 64-43237 (U.S. patent application No. 228,590) discloses an apparatus employing an alternate scan method as a method of solving such a problem.

In this method, the scanning order of an ultrasonic beam is changed, as shown in FIGS. 3A and 3B.

Referring to FIG. 3A, when an ultrasonic transmission beam is to be scanned from the right end of a sector region to be scanned by an ultrasonic transducer 1, the scanning order is first the first right beam scanning line (No. 1), then the second beam scanning line (No. 2), the third beam scanning line (No. 3), the fourth beam scanning line (No. 4), the first beam scanning line (No. 1), the second beam scanning line (No. 2), the third beam scanning line (No. 3), .... That is, block scan is performed every four beam scanning lines. In this case, the repetition frequency fr of an ultrasonic transmission beam in the same direction is given by:

$$fr = fr'/4 \qquad (6)$$

As is apparent from equation (3), if the method shown in FIG. 3A is employed, the lower limit fdmin of measurable flow velocity can be reduced to ¼ that of the conventional method, i.e., transmitting an ultrasonic pulse n times in a first beam direction, and sequentially transmitting an ultrasonic pulse n times in the adjacent beam directions.

In this case, according to the method shown in FIG. 3A, if the number of ultrasonic transmission operations in the same beam direction (the number of sampling operations of Doppler signals) is represented by n, n =8. If, however, eight data are read out from a memory (not shown) for each beam scanning line, since block scan is performed every four beam scanning lines, as shown in FIG. 3B, the time phase differences among the respective blocks are large, resulting in a discontinuous image within one frame.

As a method of reducing the above-mentioned time phase difference, the above-described patent application also discloses an alternate constant-interval scan method as shown in FIGS. 4A to 4C. In this method, a plurality of ultrasonic beam scanning lines are sequentially scanned as a group, and group scanning is performed by sequentially changing the ultrasonic beam scanning lines selected as the group while performing sequential scanning within the group, thus performing beam scanning of the entire scanning region. The scanning direction of the ultrasonic beam scanning lines in each group is the same as the scanning direction of group scanning performed by sequential changes in selection of groups. When scanning is to be performed from the right end of a transducer 1 in FIG. 4A, the scanning order is first a beam scanning line No. 1, then a beam scanning line No. 2, a beam scanning line No. 3, a beam scanning line No. 4, a beam scanning line No. 1, then a beam scanning line No. 2, a beam scanning line No. 3, a beam scanning line No. 4, ... (No ultrasonic wave is actually transmitted to "dummy" portions. However, for the sake of easy understanding, a description of the "dummy" portions is omitted, and this scan method will be described after the "dummy" portion), as shown in FIGS. 4A and 4C. Although no ultrasonic wave is actually transmitted to the "dummy" portions in FIG. 4A, scanning is performed at corresponding timings. With this operation, similar to the case shown in FIGS. 3A and 3B, the repetition frequency of an ultrasonic beam (the sampling frequency for Doppler signals) fr in the same beam direction can be reduced to ¼ that of the conventional apparatus. In addition, since the output timings of Doppler data can be set at equal intervals, the time phase differences in one frame can be set to be uniform.

Even in such a method, however, the following problem is posed. Assume that a significantly reflecting substance by which a ultrasonic wave is significantly reflected is present outside the depth of view field. In this case, as shown in FIGS. 4A, 5A, and 5B, since the ultrasonic beam direction of the immediately preceding scanning is changed at the end of a plurality of sampling operations in the same beam direction, an echo signal from outside the depth of view field may enter the next rate period (scanning period). For this reason the echo signal becomes a residual echo signal and is regarded as a phase difference, thus producing a color artifact Q in the depth of view field. For example, in the case shown in FIGS. 4A to 4C, since the rate immediately before the ultrasonic beam scanning line No. 3 may coincide with that of the beam scanning line No. 2, No. 6, or No. 7, a phase difference is generated due to the residual echo. This phase difference becomes a Doppler signal to produce an artifact, resulting in poor image quality.

SUMMARY OF THE INVENTION

It is, therefore, an object of the present invention to provide an ultrasonic diagnosing apparatus which ca greatly reduce an artifact by eliminating the influences of a residual echo, and can obtain an excellent ultrasonic image.

According to the present invention, there is provided an ultrasonic diagnosing apparatus for performing transmission/reception of an ultrasonic wave with respect to an object to be examined by using an ultrasonic transducer, detecting a Doppler shift signal from a reception signal, and displaying ultrasonic data based on the data obtained by frequency-analyzing the Doppler shift signal. The apparatus includes a control section. The control section controls at least a transmitter/receiver so as to sequentially scan a plurality of ultrasonic beam scanning lines as a group. In addition, the control section performs group scanning by sequentially changing the ultrasonic beam scanning lines selected as the group while repeating sequential scanning within the group, thus performing beam scanning of the entire scanning region, thereby decreasing the sampling frequency for Doppler data without changing the pulse repetition frequency, and reversing the scanning order of the ultrasonic beam in the group with respect to the group scanning direction of the ultrasonic beam IU scanning lines selected as the group.

According to the ultrasonic diagnosing apparatus of the present invention, since the scanning order of an ultrasonic beam sequentially scanned within a group is reversed to the group scanning direction, if, for example, a four-step alternate scan method is employed, a beam scanning line No. 5 is mainly scanned before a beam scanning line No. 4, and a residual echo can be reduced. The first three data obtained from a beam scanning line No. 1 before the beam scanning line No. 4 is small in amount compared with the total data. Furthermore, since these data constitute an initial portion, they can be easily neglected in data processing, thus easily reducing a residual echo accordingly. Therefore, artifacts can be greatly reduced, and an excellent ultrasonic image can be obtained.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

FIGS. 3A and 3B and FIGS. 4A to 4C are views for explaining alternate scan methods of conventional ultrasonic diagnosing apparatuses;

DETAILED DESCRIPTION OF THE PREFERRED EMBODIMENTS

Figure 1:
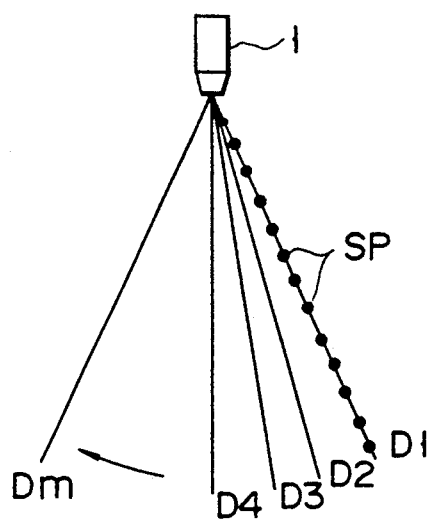
FIG. 1 is a schematic view showing a scan pattern employed by a conventional ultrasonic diagnosing apparatus.
Figure 2:
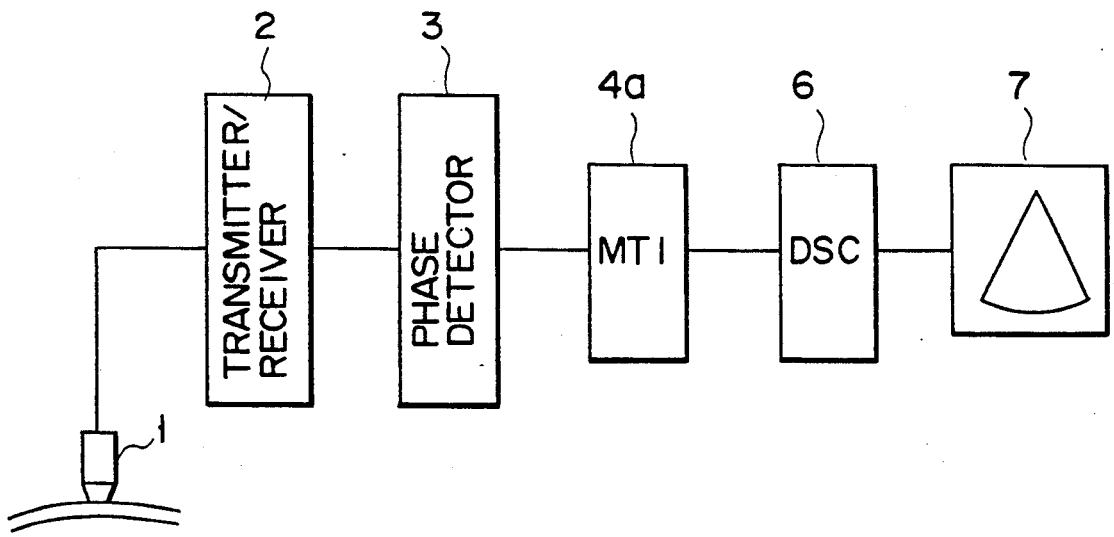
FIG. 2 is a block diagram showing a schematic arrangement of the conventional ultrasonic diagnosing apparatus.
Figure 4A:
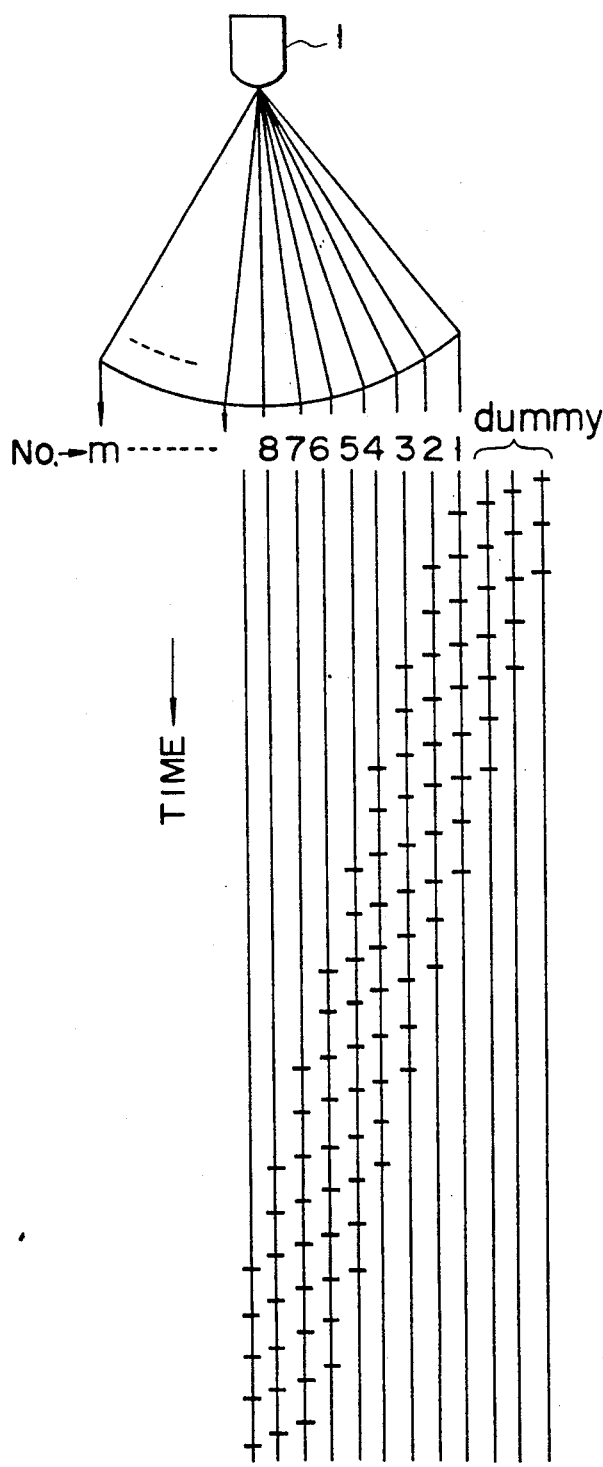
Figure 4B:
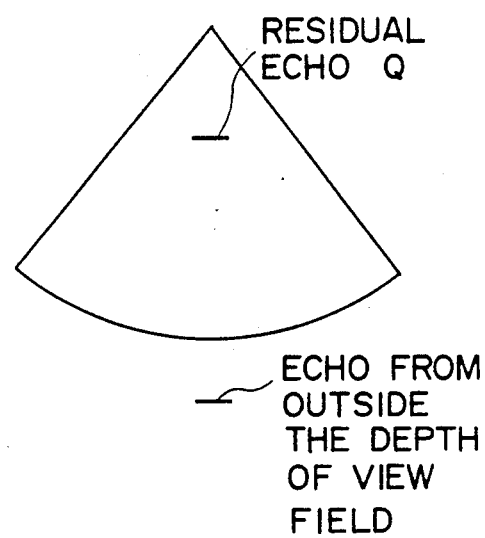
Figure 4C:
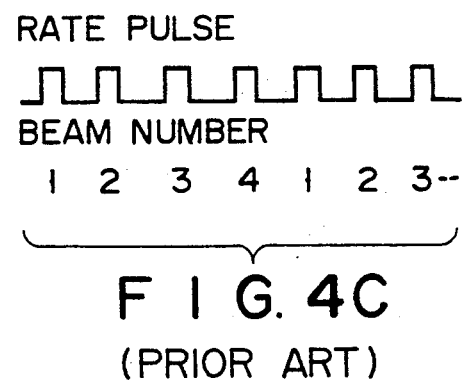
Figure 5A:
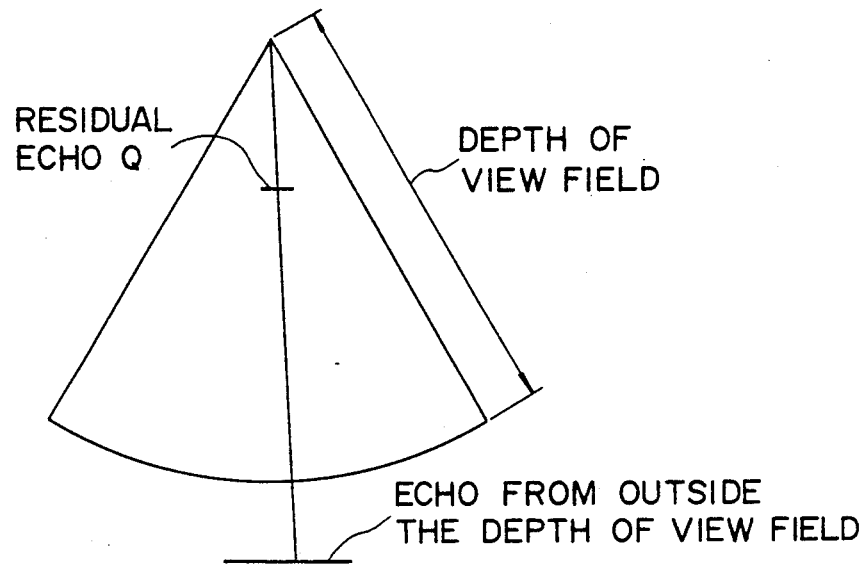
FIGS. 5A and 5B are views for explaining an artifact due to a residual echo in the conventional apparatus.
Figure 5B:
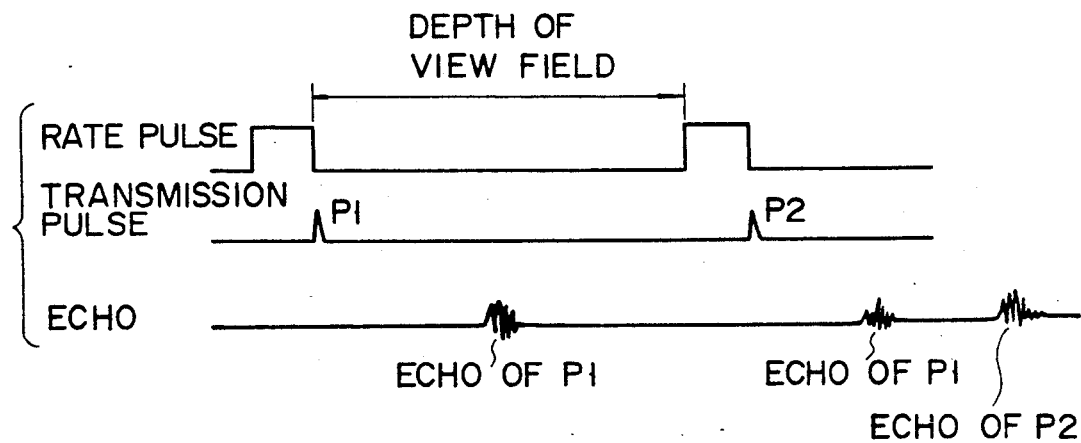
Figure 6:
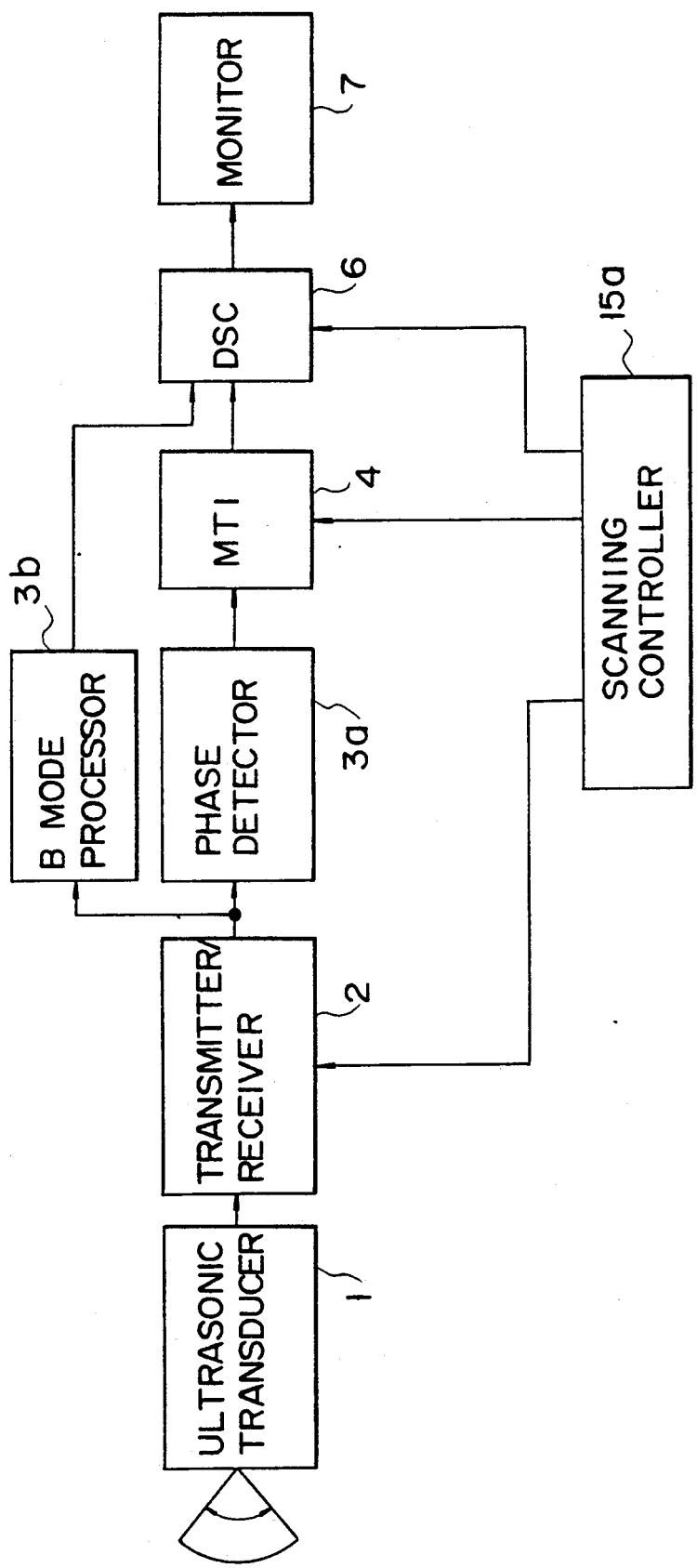
FIG. 6 is a block diagram showing a schematic arrangement of an ultrasonic diagnosing apparatus according to an embodiment of the present invention.
Figure 7A:
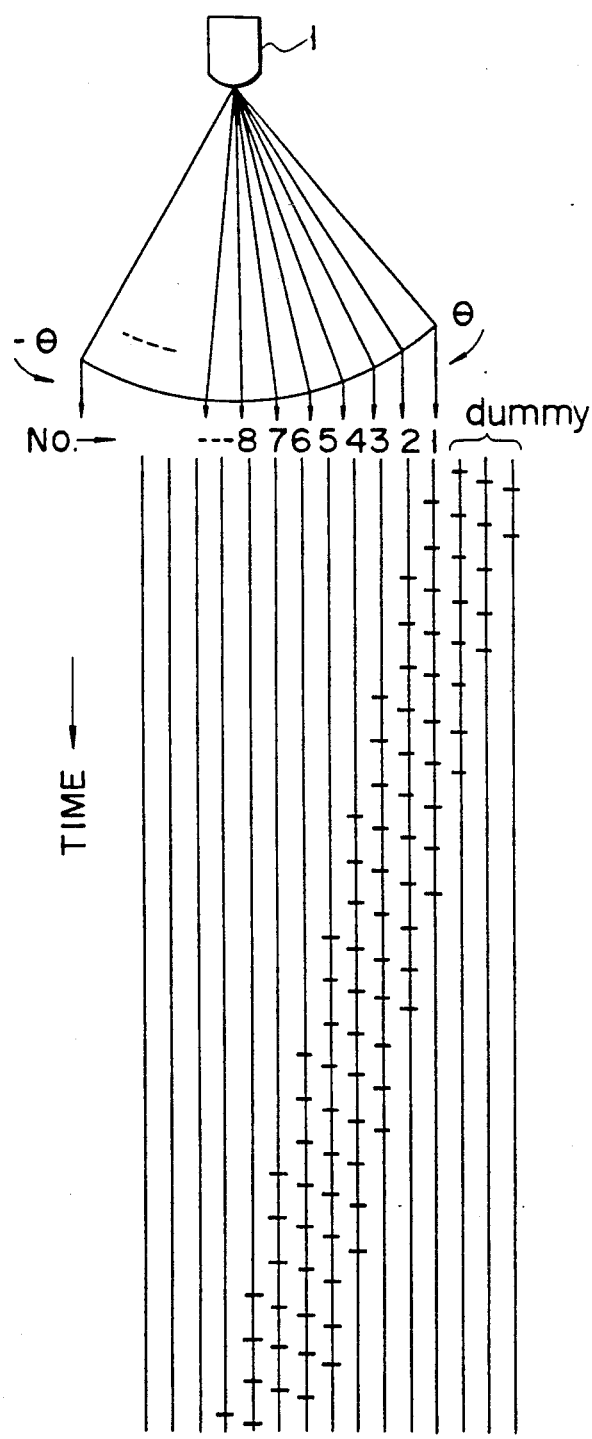
FIGS. 7A to 7C are views for explaining an alternate four-step scan method employed by the apparatus in FIG. 6.
Figure 7B:
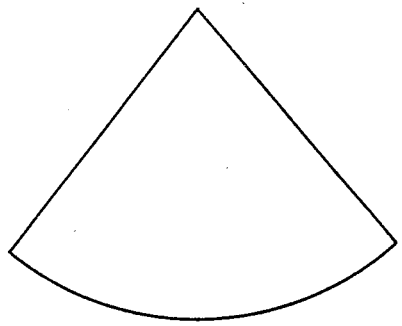
Figure 7C:
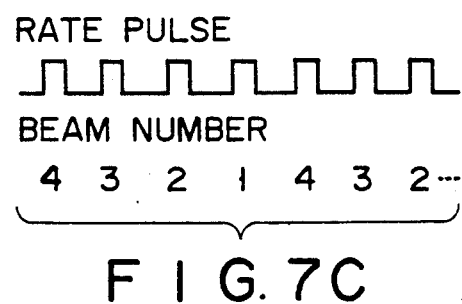

FIG. 6 shows an arrangement of an ultrasonic diagnosing apparatus according to an embodiment of the present invention. FIGS. 7A to 7C show a four-step alternate scan performed by the apparatus shown in FIG. 6. The same reference numerals in FIGS. 6 and 7A to 7C denote the same parts as those in FIGS. 1, 5A, and 5B, and a detailed description thereof will be omitted.

The characteristic feature of the apparatus shown in FIG. 6 is that the sampling frequency for Doppler data is reduced to $\frac{1}{4}$ that of the conventional apparatus by controlling a transmitter/receiver 2 and an MTI circuit 4 without changing the pulse repetition frequency, and that a scanning controller 15a is arranged to convert the scanning order of an ultrasonic beam, which is transmitted/received a plurality of times within a group, into a scanning order coinciding with a direction ($-\theta$ direction) reverse to a group scanning direction $\theta$.

That is, as shown in FIGS. 7A to 7C, the scanning order of a ultrasonic beam within a group coincides with a direction ($-\theta$ direction) reverse to the group scanning direction $\theta$. As shown in FIG. 7A to 7C, four-step scan is alternately performed in the following order: a beam scanning line No. 4, a beam scanning line No. 3, a beam scanning line No. 2, a beam scanning line No. 1, a beam scanning line No. 4, a beam scanning line No. 3, a beam scanning line No. 2, a beam scanning line No. 1, a beam scanning line No. 4, a beam scanning line No. 3, a beam scanning line No. 2, a beam scanning line No. 5, a beam scanning line No. 4, a beam scanning line No. 3, Referring to FIG. 6, an ultrasonic transducer 1 serves to transmit/receive an ultrasonic pulse to/from an object to be examined. The transmitter/receiver 2 drives the ultrasonic transducer 1 to generate an ultrasonic wave, and receives the ultrasonic wave reflected by the object. A phase detector 3a phase-detects the reception signal of the transmitter/receiver 2 to obtain a Doppler shift signal. A B mode processor 3b forms a B-mode image from the reception signal of the transmitter/receiver 2, converts the B-mode image into a digital signal, and outputs it to a DSC 6. The MTI circuit 4 converts the signal from the phase detector 3a into a digital signal, and extracts only a Doppler signal by filtering. In addition, the MTI circuit 4 calculates the average velocity, turbulence, and power of a blood flow. The signals from the B mode processor 3b and the MTI circuit 4 are written in the DSC 6. These signals are subjected to scan conversion according to, e.g., a TV (television) scan scheme and are read out to be converted into analog signals. The analog signals are then output to a monitor 7.

An operation of the ultrasonic diagnosing apparatus having the above-described arrangement will be described below.

As shown in FIG. 6, control signals are supplied from the scanning controller 15a to the transmitter/receiver 2 and the MTI circuit 4. The ultrasonic transducer 1 is driven by the transmitter/receiver 2, and an ultrasonic pulse is transmitted from the ultrasonic transducer 1 a predetermined number of times. The ultrasonic wave scanning order in the group of the transducer 1 coincides with the direction $-\theta$ reverse to the group scanning direction $\theta$. That is, as shown in FIGS. 7A to 7C, the scanning order is first the beam scanning line No. 4, then the beam scanning line No. 3, the beam scanning line No. 2, the beam scanning order No. 1, the beam scanning order No. 4, the beam scanning order No. 3, the beam scanning order No. 2, ....

The ultrasonic wave reflected by a living body is received by the transmitter/receiver 2 through the ultrasonic transducer 1. The wave is then detected by the phase detector 3a to obtain a detected signal consisting of a Doppler shift signal and a clutter component as an unwanted low-frequency component. This detected signal is supplied to the MTI circuit 4. In the MTI circuit 4, the detected signal is converted into a digital signal by an A/D (analog-to-digital) converter, and the clutter component is removed by an MTI filter. In addition, the Doppler shift signal based on a blood flow is frequency-analyzed by a frequency analyzer so as to obtain Doppler data including Doppler velocity, turbulence, and power data. These data are written in a frame memory of the DSC 6 upon predetermined color processing. When data (e.g., n=8) are obtained for each beam scanning line, eight data are read out from the DSC 6 for each beam scanning line and are output to the monitor 7 as blood flow data.

In this manner, in the above-described alternate four-step scan method, since the ultrasonic wave scanning direction in the group is set to coincide with the direction $-\theta$ reverse to the group scanning direction $\theta$, the beam scanning line No. 5 is mainly scanned before the beam scanning line No. 4, and a residual echo is reduced. In addition, since the several data initially obtained from the beam scanning line No. 1 before the beam scanning line No. 4 is small compared with the total number of data, a residual echo can be reduced accordingly. Furthermore, the initially obtained data are poor in effectiveness because of the excessive response properties of the MTI filter as a digital filter in the MTI circuit 4, and hence are not normally used. By slightly increasing these non-used data in number to the range of the above-mentioned several initial data, the influences of a residual echo can be effectively eliminated. Therefore, a color artifact can be easily and effectively reduced. Furthermore, since the pulse repetition frequency (the sampling frequency for Doppler signals) fr in the same beam direction can be reduced to ¼ that of the conventional apparatus, an excellent ultrasonic image can be obtained without sacrificing the maximum depth of view field, the number of frames, and the image quality.

The scanning order of an ultrasonic beam shown in FIG. 7A will be shown in detail: No. 1, (dummy), (dummy), (dummy), No. 1, (dummy), (dummy), No. 2, No. 1, (dummy), (dummy), No. 2, No. 1, (dummy), (dummy), No. 2, No. 1, (dummy), No. 3, No. 2, No. 1, (dummy), No. 3, No. 2, No. 1, (dummy), No. 3, No. 2, No. 1, No. 4, No. 3, No. 2, No. 1, No. 4, No. 3, No. 2, 1 No. 1, No. 4, No. 3, No. 2, No. 5, No. 4, No. 3, No. 2, No. 5, No. 4, No. 3, No. 2, No. 5, No. 4, No. 3, ....

In place of the above-described scanning order, for example, the following scanning orders may be employed on substantially the same principle as described above:

(a) No. 1, (dummy), (dummy), (dummy), No. 2, No. 1, (dummy), (dummy), No. 2, No. 2, No. 1, (dummy), No. 4, No. 3, No. 2, No. 1, No. 5, No. 4, No. 3, No. 2, No. 6, ....

(b) No. 1, (dummy), (dummy), (dummy), No. 1, (dummy), (dummy), No. 2, No. 1, (dummy), (dummy), No. 2, No. 1, (dummy), No. 3, No. 2, No. 1, (dummy), No. 3, No. 2, No. 1, No. 4, No. 3, No. 2, No. 1, No. 4, No. 3, No. 2, No. 5, No. 4, No. 3, NO. 2, No. 5, No. 4, No. 3, ....

(c) No. 1, (dummy), (dummy), (dummy), No. 1, (dummy), (dummy), (dummy), No. 2, No. 1, (dummy), (dummy), No. 2, No. 1, (dummy), (dummy), No. 3, No. 2, No. 1, (dummy), No. 3, No. 2, No. 1, (dummy), No. 4, No. 3, No. 2, No. 1, No. 4, No. 3, No. 2, No. 1, No. 5, No. 4, No. 3, No. 2, No. 5, No. 4, No. 3, No. 2, No. 6, No. 5, No. 4, ....

The present invention is not limited to the above-described embodiment. In the above embodiment, the alternate four-step scan method is described. However, alternate scan methods with steps other than four steps may be employed. In addition, the present invention is not limited to the sector scan method but may be applied to the linear scan method. It is apparent that various changes and modifications can be made within the spirit and scope of the invention.

Additional advantages and modifications will readily occur to those skilled in the art. Therefore, the invention in its broader aspects is not limited to the specific details and representative devices shown and described herein. Accordingly, various modifications may be made without departing from the spirit or scope of the general inventive concept as defined by the appended claims and their equivalents.

What is claimed is:

1. An ultrasonic diagnosing apparatus comprising:
   an ultrasonic transducer for converting an electrical signal into a sound wave and converting the sound wave into an electrical signal;
   transmitting/receiving means for controlling said ultrasonic transducer to transmit an ultrasonic wave to an object to be examined and to receive a reflected ultrasonic wave from the object as an ultrasonic echo;
   scanning control means for scanning a predetermined scanning region of the object by transmitting and receiving the ultrasonic wave with respect to a plurality of ultrasonic beam scanning lines by controlling at least one of said ultrasonic transducer and said transmitting/receiving means such that each scanning line is scanned a predetermined number of times, each scanning line being scanned after a first adjacent scanning line, adjacent to the each scanning line in a first direction, is scanned at an initial period of the scanning for the predetermined number, and each scanning line being scanned after a second adjacent scanning line, next to the each scanning line in a second direction opposite to the first direction, is scanned, for the rest of the scanning for the predetermined number of times;
   phase detecting means for extracting a Doppler shift signal from a reception signal obtained by said transmitting/receiving means;
   Doppler data processing means for obtaining Doppler data by processing the Doppler shift signal extracted by said phase detecting means, said Doppler data processing means including means for neglecting a predetermined number of initial Doppler data repeatedly sampled at the same sampling point and obtained after the scanning of the first adjacent scanning line; and
   display means for displaying an image based on the Doppler data obtained by said Doppler data processor means.

2. An apparatus according to claim 1, wherein said ultrasonic transducer comprises an array transducer constituted by a plurality of transducer elements.

3. An apparatus according to claim 2, wherein said scanning control means includes control means for sector electronic scan.

4. An apparatus according to claim 2, wherein said scanning control means includes control means for linear electronic scan.

5. An apparatus according to claim 1, wherein said scanning control means includes means for changing the ultrasonic beam scanning lines selected as the group for every scanning operation within the same group.

6. An apparatus according to claim 1, wherein said scanning control means includes means for changing the ultrasonic beam scanning lines selected as the group in units of a plurality of repetitive scanning operations within the same group.

7. An apparatus according to claim 1, wherein said scanning control means includes means for changing the number of ultrasonic beam scanning lines selected as the group around the time when the ultrasonic beam scanning lines selected as the group are changed.

8. An apparatus according to claim 1, wherein said scanning control means includes means for always selecting a predetermined number of ultrasonic beam scanning lines as the group of ultrasonic beam scanning lines.

9. An apparatus according to claim 1 wherein said first direction is a direction of group scanning and said second direction is opposite to a direction of group scanning.

10. An apparatus as in claim 1 wherein a number of lines scanned during said initial period of smaller than a number of lines scanned during the rest of the scanning period.

11. An apparatus as in claim 10 wherein the number of scanning lines during said initial period is not constant.

12. An ultrasonic diagnosing apparatus comprising:
   an ultrasonic transducer for converting an electrical signal into a sound wave and converting the sound wave into an electrical signal;
   transmitting/receiving means for controlling said ultrasonic transducer to transmit an ultrasonic wave to an object to be examined and receive an ultrasonic wave reflected by the object as an ultrasonic echo;
   scanning control means for scanning a predetermined scanning region of the object by transmitting and receiving the ultrasonic wave with respect to a plurality of ultrasonic beam scanning lines by controlling at least one of said ultrasonic transducer and said transmitting/receiving means such that each scanning line is scanned a predetermined number of times, each scanning line being scanned after a first adjacent scanning line, adjacent to the each scanning line in a first direction, is scanned at an initial period of the scanning for the predetermined number, and each scanning line being scanned after a second adjacent scanning line, next to the each scanning line in a second direction opposite to the first direction, is scanned, for the rest of the scanning for the predetermined number of times;
   phase detecting means for extracting a Doppler shift signal from a reception signal obtained by said transmitting/receiving means;
   Doppler data processing means for obtaining Doppler data by processing the Doppler shift signal extracted by said phase detecting means, said Doppler data processing means including means for neglecting a predetermined number of initial Doppler data repeatedly sampled at the same sampling point and obtained after the scanning of the first adjacent scanning line;
   ultrasonic image processing means for obtaining an ultrasonic image data by processing the reception signal obtained by said transmitting/receiving means; and
   display means for displaying an image based on the ultrasonic image data obtained by said ultrasonic image processing means and the Doppler data obtained by said Doppler data processing means.

13. An apparatus according to claim 12, wherein said ultrasonic transducer comprises an array transducer constituted by a plurality of transducer elements.

14. An apparatus according to claim 13, wherein said scanning control means includes control means for sector electronic scan.

15. An apparatus according to claim 13, wherein said scanning control means includes control means for linear electronic scan.

16. An apparatus according to claim 12, wherein said scanning control means includes mean for changing the ultrasonic beam scanning lines selected as the group for every scanning operation within the same group.

17. An apparatus according to claim 12, wherein said scanning control means includes means for changing the ultrasonic beam scanning lines selected as the group in units of a plurality of repetitive scanning operations within the same group.

18. An apparatus according to claim 12, wherein said scanning control means includes means for changing the number of ultrasonic beam scanning lines selected as the group around the time when the ultrasonic beam scanning lines selected as the group are changed.

19. An apparatus according to claim 12, wherein said scanning control means includes means for always selecting a predetermined number of ultrasonic beam scanning lines as the group of ultrasonic beam scanning lines.

20. An apparatus according to claim 12, wherein said ultrasonic image processing means includes means for obtaining an ultrasonic B-mode image.

21. An apparatus according to claim 12, wherein said ultrasonic image processing means includes means for obtaining an ultrasonic M-mode image.

22. An apparatus according to claim 12 wherein said first direction is a direction of group scanning and said second direction is opposite to a direction of group scanning.

23. An apparatus as in claim 12 wherein a number of lines scanned during said initial period is smaller than a number of lines scanned during the rest of the scanning period.

24. An apparatus as in claim 23 wherein the number of scanning lines during said initial period is not constant.

* * * * *